(12) United States Patent
Jiang et al.

(10) Patent No.: US 10,987,518 B2
(45) Date of Patent: Apr. 27, 2021

(54) TERMINATING PACEMAKER MEDIATED TACHYCARDIA (PMT) IN DUAL CHAMBER LEADLESS PACEMAKER SYSTEMS

(71) Applicant: Pacesetter, Inc., Santa Clara, CA (US)

(72) Inventors: Chunlan Jiang, Northridge, CA (US); Matthew G. Fishler, Scotts Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 238 days.

(21) Appl. No.: 16/238,850

(22) Filed: Jan. 3, 2019

(65) Prior Publication Data
US 2020/0215340 A1    Jul. 9, 2020

(51) Int. Cl.
*A61N 1/362*   (2006.01)
*A61N 1/372*   (2006.01)
*A61N 1/375*   (2006.01)

(52) U.S. Cl.
CPC ....... *A61N 1/37288* (2013.01); *A61N 1/3622* (2013.01); *A61N 1/3756* (2013.01); *A61N 1/37512* (2017.08)

(58) Field of Classification Search
None
See application file for complete search history.

(56) References Cited

U.S. PATENT DOCUMENTS

| | | |
|---|---|---|
| 4,539,991 A | 9/1985 | Boute et al. |
| 5,228,438 A | 7/1993 | Buchanan |
| 5,312,450 A | 5/1994 | Markowitz |
| 5,423,868 A | 6/1995 | Nappholz et al. |
| 5,496,350 A | 3/1996 | Lu |
| 5,507,783 A | 4/1996 | Buchanan |
| 5,609,610 A | 3/1997 | Nappholz |
| 5,674,255 A | 10/1997 | Walmsley et al. |
| 7,509,168 B1 | 3/2009 | Mengotto et al. |
| 9,216,298 B2 | 12/2015 | Jacobson |
| 9,522,280 B2 | 12/2016 | Fishier et al. |
| 2002/0123769 A1 | 9/2002 | Panken et al. |

(Continued)

OTHER PUBLICATIONS

International Search Report & The Written Opinion of the International Searching Authority dated Dec. 16, 2019, International Application No. PCT/US2019/053587.

(Continued)

*Primary Examiner* — Erica S Lee
(74) *Attorney, Agent, or Firm* — Vierra Magen Marcus LLP

(57) ABSTRACT

An implantable system including an atrial leadless pacemaker (aLP) and a ventricular leadless pacemaker (vLP), and methods for use therewith, are configured or used to terminate a pacemaker mediated tachycardia (PMT). One of the aLP or the vLP detects a PMT and informs the other one. The aLP initiates a PMT PA interval that is shorter than a PA interval that the aLP would otherwise use for atrial pacing if a PMT was not detected. The vLP initiates a PMT PV interval that is longer than the PMT PA interval. If an intrinsic atrial or ventricular event is detected before PMT PA interval or the PMT PV interval expires, then these intervals will be terminated, otherwise an atrial chamber will be paced if the PMT PA interval expires, and/or a ventricular chamber will be paced if the PMT PV interval expires. This should have the effect of terminating the PMT.

20 Claims, 11 Drawing Sheets

(56) References Cited

U.S. PATENT DOCUMENTS

2008/0255627 A1    10/2008  Bjorling
2016/0121128 A1*   5/2016   Fishier ............... A61N 1/37288
                                                              607/14
2017/0106191 A1*   4/2017   Pei ....................... A61N 1/3622
2018/0117324 A1    5/2018   Schilling et al.

OTHER PUBLICATIONS

Monteil, Benjamin, et al., "Pacemaker-Mediated Tachycardia: Manufacturer Specifics and Spectrum of Cases: Pacemaker-Mediated Tachycardia," PACE-Pacing and Clinical Electrophysiology, vol. 38, No. 12, Dec. 1, 2015, pp. 1489-1498.
Sergio, Richter, et al., "Ventriculoatrial conduction and related pacemaker-mediated arrhythmias in patients implanted for atrioventricular block: An old problem revisited," International Journal of Cardiology, Elsevier, Amsterdam, NL, vol. 168, No. 4, Apr. 29, 2013, pp. 3300-3308.
Alasti, Mohammad, et al., "Pacemaker-mediated arrhythmias," Journal of Arrhythmia, vol. 34, No. 5, Aug. 3, 208, pp. 485-492.

\* cited by examiner

TERMINATING PACEMAKER MEDIATED TACHYCARDIA (PMT) IN DUAL CHAMBER LEADLESS PACEMAKER SYSTEMS

FIELD OF TECHNOLOGY

Embodiments described herein generally relate to dual chamber leadless pacemaker systems, and methods for use therewith, that can terminate a pacemaker mediated tachycardia (PMT).

BACKGROUND

A pacemaker-mediated tachycardia (PMT), also referred to as endless loop tachycardia, or a pacemaker reentrant tachycardia, occurs when a pacemaker system paces a ventricle at an inappropriately fast rate for a sustained period of time. PMT occurs when a ventricular event occurs at a time during which the connective tissue between the atrium and ventricle can transmit retrograde electrical signals from the ventricle to the atrium. The conduction of the ventricular signal to the atrium provides a spurious electrical signal in the atrium that is considered to be a natural atrial event by the pacemaker system. The pacemaker system senses the spurious retrograde atrial signal and then paces the ventricle at a programmed atrioventricular (AV) time period (also known as (aka) an AV interval or an AV delay) following the signal. The paced ventricular signal is conducted to the atrium and is again erroneously detected by the pacemaker system as a natural atrial event. The pacemaker system therefore continues to pace the ventricle at a relatively high rate defined by the sum of the programmed AV interval and the retrograde conduction time between the ventricle and atrium. The high rate is sustained indefinitely by the pacemaker system, because retrograde conduction ensures that the pacemaker system detects what appears to be high rate atrial events and tracks these spurious atrial events by generating corresponding high rate ventricular paces. A PMT can be caused, e.g., by a retrograde conduction that follows a premature ventricular contractions (PVC), or by another event that causes atrioventricular (AV) synchrony to be dissociated.

Explained another way, ventricular events which are conducted in a retrograde direction to the atria cause atrial depolarizations. The pacemaker system senses this retrograde atrial depolarization and then, after the appropriate AV interval (e.g., aka an AV delay), delivers a stimulus to the ventricle. Thus, the pacemaker system provides the antegrade conduction pathway for a reentrant circuit and the intrinsic conduction system of the heart provides the retrograde pathway. A repetitive cycle of ventricular retrograde P-wave synchronized pacing can then ensue, which is the PMT.

There are existing PMT termination techniques for use with conventional dual chamber pacemaker systems that include a subcutaneous pacemaker housing (aka a "can" or "case") and leads that include electrodes within the right atrium and the right ventricle. For example, in a conventional dual chamber pacemaker system, once a PMT is detected it can be terminated by extending the post ventricular atrial refractory (PVARP) long enough such that the retrograde P-wave is not tracked and the reentrant circuit is broken. Another method for terminating PMT is by restarting the AV cycle, and more specifically, by delivering an atrial pacing output at a fixed time after the retrograde P-wave. However, such existing PMT termination techniques cannot be applied directly to a leadless dual chamber pacemaker system due to the additional complications associated with two physically-independent atrial and ventricular pacing units.

SUMMARY

Embodiments of the present technology relate to dual chamber leadless pacemaker systems, and methods for use therewith, that can be used to terminate a PMT. In accordance with certain embodiments, the dual chamber leadless pacemaker system, which can also be referred to more generally as an implantable system, includes an atrial leadless pacemaker (aLP) and a ventricular leadless pacemaker (vLP). The aLP is configured to be implanted within or on an atrial cardiac chamber. The vLP is configured to be implanted within or on a ventricular cardiac chamber. The aLP and the vLP are capable of performing implant-to-implant (i2i) communication with one another.

Certain methods involve one of the aLP or the vLP detecting a PMT, and informing the other one (via an i2i communication) that the PMT was detected. The aLP, in response to the PMT being detected, initiates a PMT PA interval that is shorter than a PA interval that the aLP would otherwise use for atrial pacing if a PMT was not detected. The vLP, in response to the PMT being detected, initiates a PMT PV interval that is longer than the PMT PA interval.

Such a method can also involve the aLP, in response to the PMT PA interval expiring (without an intrinsic atrial event being detected during the PMT PA interval), pacing the atrial cardiac chamber, and informing the vLP (via an i2i communication) of the pacing the atrial cardiac chamber. The vLP, in response to receiving the i2i communication from the aLP that informs the vLP of the pacing the atrial cardiac chamber, terminates the PMT PV interval and initiates an AV interval.

Such a method can alternatively involve the aLP, in response to an intrinsic atrial event being detected during the PMT PA interval, terminating the PMT PA interval, and informing the vLP (via an i2i communication) of the detected intrinsic atrial event. The vLP, in response to receiving the i2i communication from the aLP (that informs the vLP of the intrinsic atrial event being detected), terminates the PMT PV interval and initiates a PV interval.

In accordance with certain embodiments, the vLP, in response to an intrinsic ventricular event being detected during the PMT PV interval, terminates the PMT PV interval, and informs the aLP (via an i2i communication) of the detected intrinsic ventricular event.

In accordance with certain embodiment, the PMT PV interval equals the PMT PA interval plus a delay, wherein the delay can either be a fixed value or a rate dependent value. The PMT PA interval can be a fixed value, or alternatively, a rate dependent value.

An implantable system, according to an embodiment of the present technology, includes an aLP and vLP. The aLP is configured to be implanted in or on an atrial cardiac chamber, and the vLP is configured to be implanted in or on a ventricular cardiac chamber. The aLP includes at least one processor, and also includes at least two electrodes that can be used for sensing an intrinsic atrial event, and pacing the atrial cardiac chamber. In certain embodiments the electrodes can be used to perform i2i communication. Alternatively, an antenna or coil can be used to perform i2i communication. Similarly, the vLP includes at least one processor, and also includes at least two electrodes that can be used for sensing an intrinsic ventricular event, and pacing the ventricular cardiac chamber. In certain embodiments the electrodes can be used to perform i2i communication. Alternatively, an antenna or coil can be used to perform i2i communication.

At least one of the aLP or the vLP is configured to detect a PMT, and in response thereto, inform the other one (via an i2i communication) that the PMT was detected. The aLP is configured to initiate a PMT PA interval, in response to the PMT being detected, wherein the PMT PA interval is shorter than a PA interval that the aLP would otherwise use for atrial pacing if a PMT was not detected. The vLP is configured to initiate a PMT PV interval, in response to the PMT being detected, wherein the PMT PV interval is longer than the PMT PA interval.

In accordance with certain embodiments, in response to the PMT PA interval expiring without an intrinsic atrial event being detected during the PMT PA interval, the aLP paces the atrial cardiac chamber and informs the vLP (via an i2i communication) of pacing the atrial cardiac chamber. The vLP, in response to receiving the i2i communication from the aLP (that informs the vLP of the pacing the atrial cardiac chamber), terminates the PMT PV interval and initiates an AV interval.

In accordance with certain embodiments, in response to an intrinsic atrial event being detected during the PMT PA interval, the aLP terminates the PMT PA interval and informs the vLP (via an i2i communication) of the detected intrinsic atrial event. The vLP, in response to receiving the i2i communication from the aLP (that informs the vLP of the intrinsic atrial event being detected), terminates the PMT PV interval and initiates a PV interval.

In accordance with certain embodiments, the vLP, in response to an intrinsic ventricular event being detected during the PMT PV interval, terminates the PMT PV interval and informs the aLP (via an i2i communication) of the detected intrinsic ventricular event.

In accordance with alternatively embodiments of the present technology, the aLP purposely suppresses sending an i2i message to the vLP in order to terminal a PMT, and more specifically, to break the PMT loop, aka, the reentrance circuit. In such an embodiments, the aLP, in response to a PMT being detected, initiates a PMT PA interval that is shorter than a PA interval that the aLP would otherwise use for atrial pacing when a PMT is not detected, and does not inform the vLP (via an i2i communication) of an atrial sensed event that caused the PMT to be detected, thereby preventing the vLP from initiating a PV interval during the PMT PA interval. The aLP terminates the PMT PA interval in response to an intrinsic atrial event being detected during the PMT PA interval, or the aLP paces the atrial cardiac chamber in response to the PMT PA interval expiring without an intrinsic atrial event being detected during the PMT PA interval. Further, the aLP informs the vLP, via an i2i communication, of an intrinsic atrial event being detected during the PMT PA interval, or of an atrial paced event being performed in response to the PMT PA interval expiring without an intrinsic atrial event being detected during the PMT PA interval.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology relate to a dual chamber leadless pacemaker system, and methods for use therewith, that can be used to terminate a pacemaker mediated tachycardia (PMT). However, before providing addition details of the specific embodiments of the present technology, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more leadless pacemakers (LPs), an implantable cardioverter-defibrillator (ICD), such as a sub-cutaneous-ICD, and/or a programmer reliably and safely coordinate pacing and/or sensing operations.

Figure 1A:
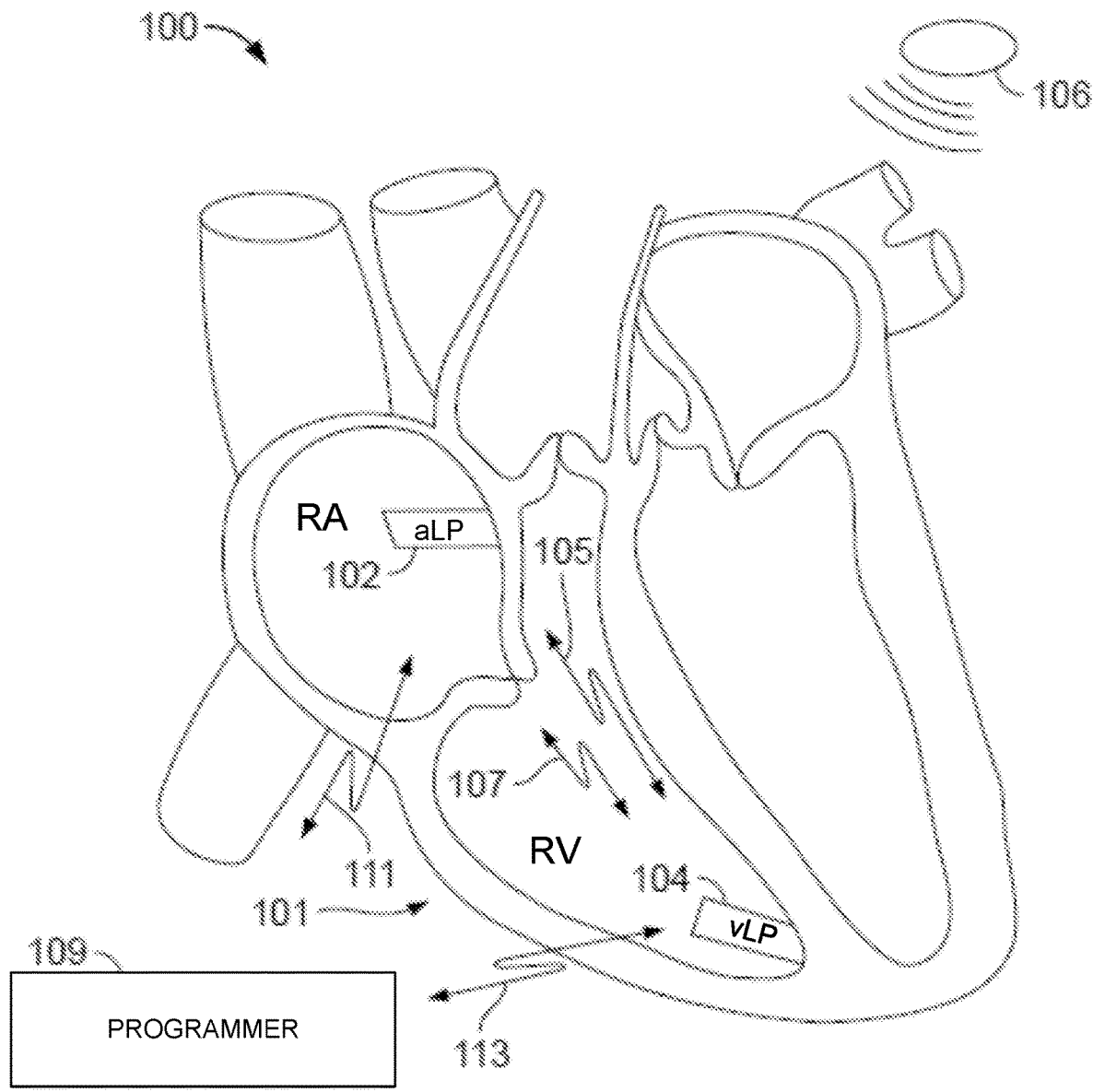
FIG. 1A illustrates a system formed in accordance with certain embodiments described herein as implanted in a heart.

FIG. 1A illustrates a system 100 formed in accordance with certain embodiments herein as implanted in a heart 101. The system 100 comprises two or more leadless pacemakers (LPs) 102 and 104 located in different chambers of the heart. LP 102 is located in a right atrium (RA), while LP 104 is located in a right ventricle (RV). The RA is also known as the right atrial chamber, and the RV is also known as the right ventricular chamber. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located. Instead of being implanted in the RA chamber, the LP 102 can be implanted on an exterior of the RA chamber. Additionally, or alternatively, instead of being implanted in the RV chamber, the LP 104 can be implanted on an exterior of the RV chamber. The LP 102 can also be referred to as an atrial leadless pacemaker (aLP) 102, and the LP 104 can also be referred to as a ventricular leadless pacemaker (vLP) 104.

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more LPs 102 and 104 can be co-implanted with the implantable cardioverter-defibrillator (ICD) 106. Each LP 102, 104 uses two or more electrodes located within, on, or within a few centimeters of the housing of the LP, for pacing and sensing at the cardiac chamber, for bidirectional communication with one another, with the programmer 109, and the ICD 106.

In accordance with certain embodiments, methods are provided for coordinating operation between LPs located in different chambers of the heart. The methods can configure a local LP to receive communications from a remote LP through conductive communication.

Figure 1B:
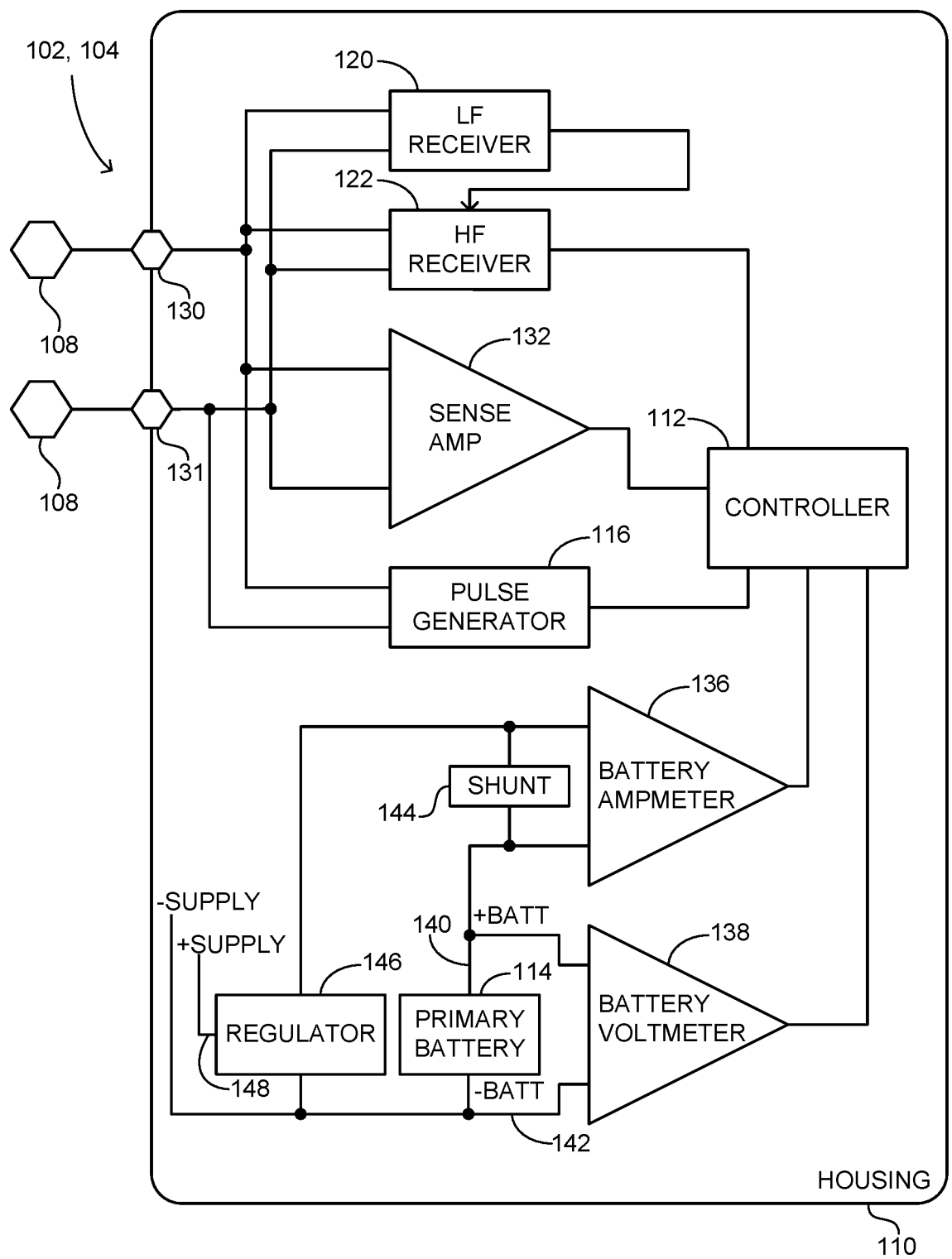
FIG. 1B is a block diagram of a single leadless pacemaker (LP) in accordance with certain embodiments herein.

Referring to FIG. 1B, a block diagram shows exemplary electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. Such timing control circuitry can also be used to control the timing of the various intervals discussed below with reference to FIGS. 5-10. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, the programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 pA. The same LP 102, 104 may implement an event message utilizing event signaling parameters for amplitude, pulse-width, pulse rate, etc. that correspond to a current draw of approximately 0.5 pA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, for sensing motion, for sensing temperature, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102, 104 and/or the ICD 106 and transmit data including designated codes for events detected or created by an individual LP. Individual LPs can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to LPs 102, 104 configured for implantation in electrical contact with a cardiac chamber and for performing cardiac rhythm management functions in combination with the implantable ICD 106. The implantable ICD 106 and the one or more LPs 102, 104 can be configured for leadless intercommunication by information conduction through body tissue and/or wireless transmission between transmitters and receivers in accordance with the discussed herein. As mentioned above, the ICD 106 can include its own motion sensor and/or temperature sensor.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, or one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs. ACap-Confirm, sensing sensitivities, etc.).

Also shown in FIG. 1B, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102, 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102, 104 can be used to sense an intracardiac electrocardiogram (IEGM) from which atrial and/or ventricular activity can be detected, e.g., by detecting QRS complexes and/or P waves. Such an IEGM can also be used by an LP 102, 104 to time when communication pulses should be generated, since the orientation of the LPs 102, 104 relative to one another can change throughout each cardiac cycle.

Figure 2:
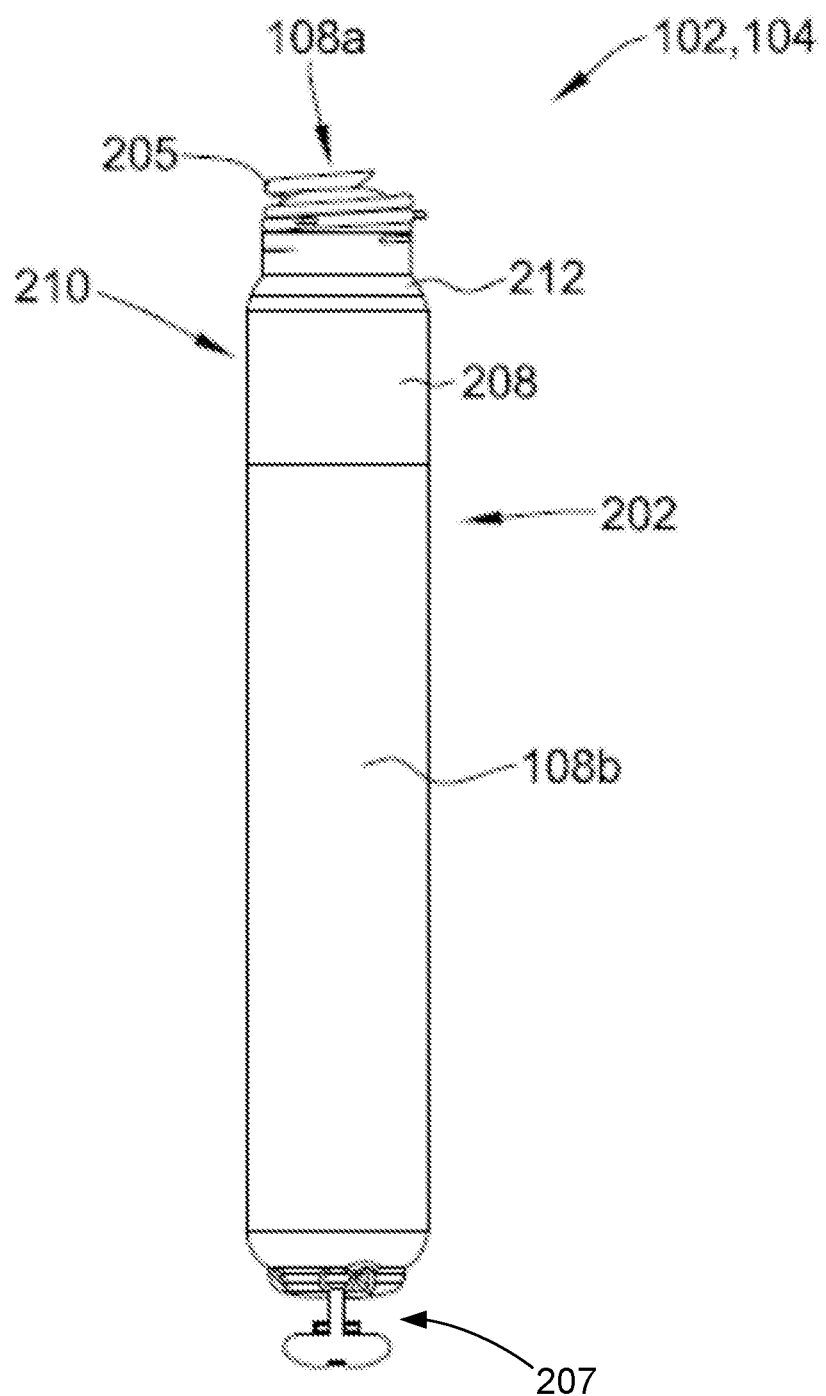
FIG. 2 illustrates an LP in accordance with certain embodiments herein.

FIG. 2 shows an LP 102, 104. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation.

The housing 202 can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 3:
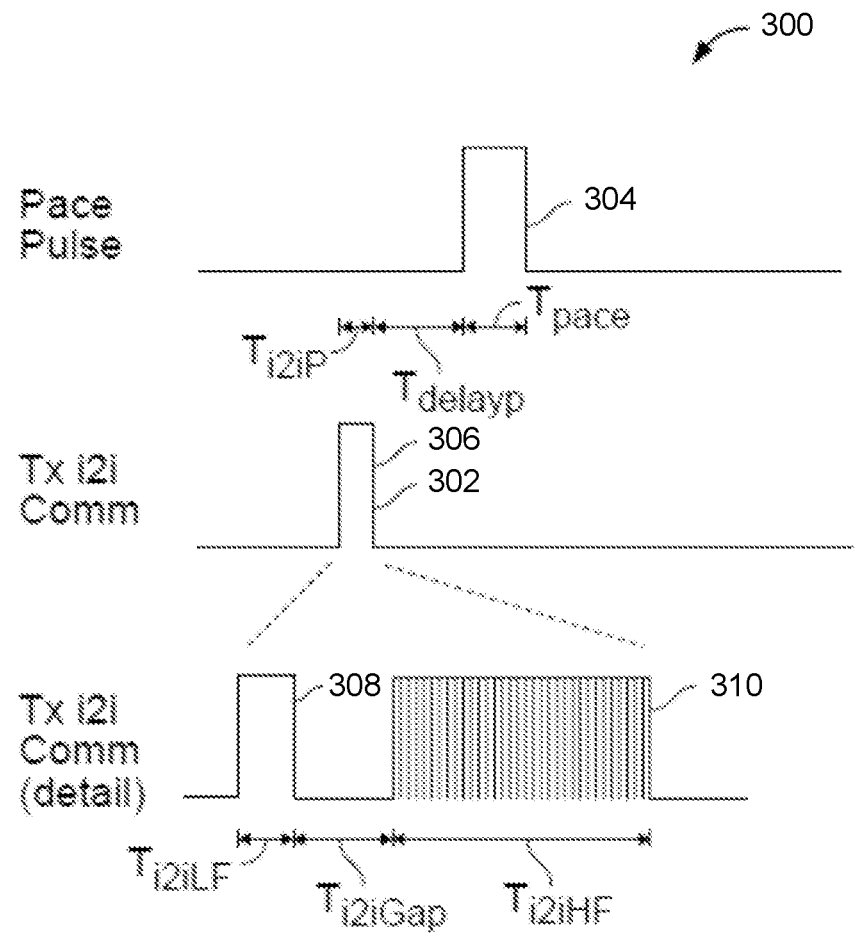
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from LP 102 to LP 104. As shown in FIG. 3, in this embodiment, an i2i transmission 302 is sent prior to delivery of a pace pulse 304 by the transmitting LP (e.g., LP 102). This enables the receiving LP (e.g., LP 104) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period $T_{i2iLF}$, and high frequency pulse train 310 lasts for a period $T_{i2iHF}$. The end of low frequency pulse 308 and the beginning of high frequency pulse train 310 are separated by a gap period, $T_{i2iGap}$.

As shown in FIG. 3, the i2i transmission 302 lasts for a period Ti2iP, and pace pulse 304 lasts for a period Tpace. The end of i2i transmission 302 and the beginning of pace pulse 304 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 4:
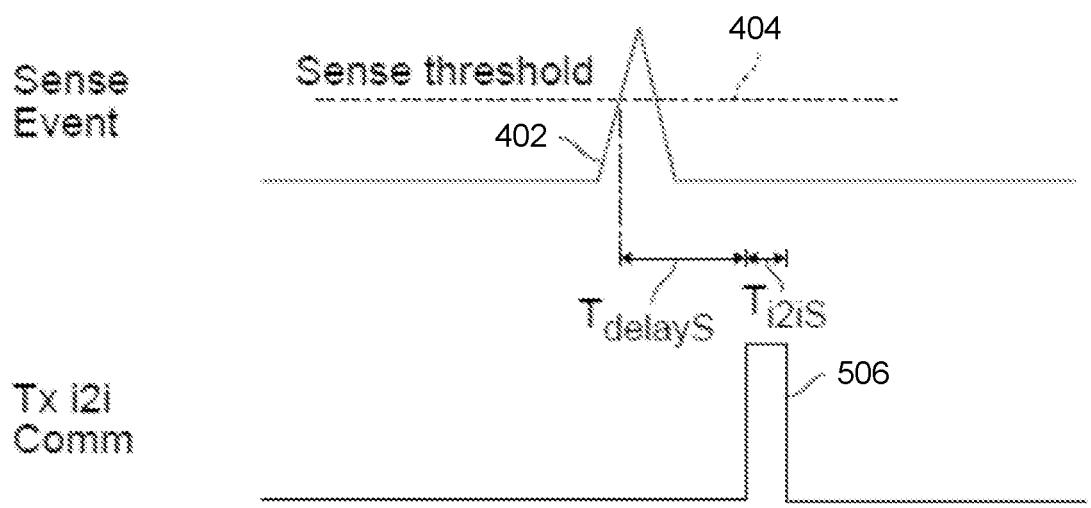
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from LP 102 to LP 104. As shown in FIG. 4, in this embodiment, the transmitting LP (e.g., LP 102) detects the sensed event when a sensed intrinsic activation 402 crosses a sense threshold 404. A predetermined delay period, $T_{delayS}$, after the detection, the transmitting LP transmits an i2i transmission 406 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 406, the envelope of i2i transmission 406 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
| --- | --- | --- |
| AS | Notification of a sensed event in atrium (if not in PVAB or PVARP) | Initiate AV interval (if not in PVAB or PVARP) |
| AP | Notification of a paced event in atrium | Initiate PAVB<br>Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

The terms i2i communication and i2i message, which are used interchangeably herein, refer to that sending of information between two implanted devices, such as between the aLP 102 and the vLP 104 discussed above with reference to FIG. 1A. Such i2i communication can be implemented as conductive communication through the same electrodes that are used for sensing cardiac activity and/or delivery of pacing therapy. Alternatively, i2i communication can be performed using telemetry coils or antennas that are used to transmit and receive wireless signals.

PMT Termination

As noted above, when using a pair of LPs (e.g., 102, 104) to perform pacing and/or sensing operations in the RA and RV, one of the challenges is terminating a pacemaker mediated tachycardia (PMT), also known as an endless-loop tachycardia, or a pacemaker reentrant tachycardia. As also noted above, PMT can result in any dual chamber pacemaker system capable of sensing and responding to atrial depolarizations when A-V synchrony is dissociated, typically by a PVC. Ventricular events are conducted in a retrograde direction to the atria that cause atrial depolarizations.

In a conventional dual chamber pacemaker system, once a PMT is detected it can be terminated by extending the PVARP long enough such that the retrograde P wave is not tracked and the reentrant circuit is broken. Another technique for terminating a PMT in a conventional dual chamber pacemaker system is by restarting the AV cycle, i.e., by delivering an atrial pacing output at a fixed time after the retrograde P-wave. However, as noted above, such existing PMT termination techniques cannot be applied directly to a leadless dual chamber pacemaker system, such as the one summarized above with reference to FIGS. 1-4, due to the additional complications associated with two physically-independent atrial and ventricular pacing units, such as the aLP 102 and the vLP 104.

Figure 5:
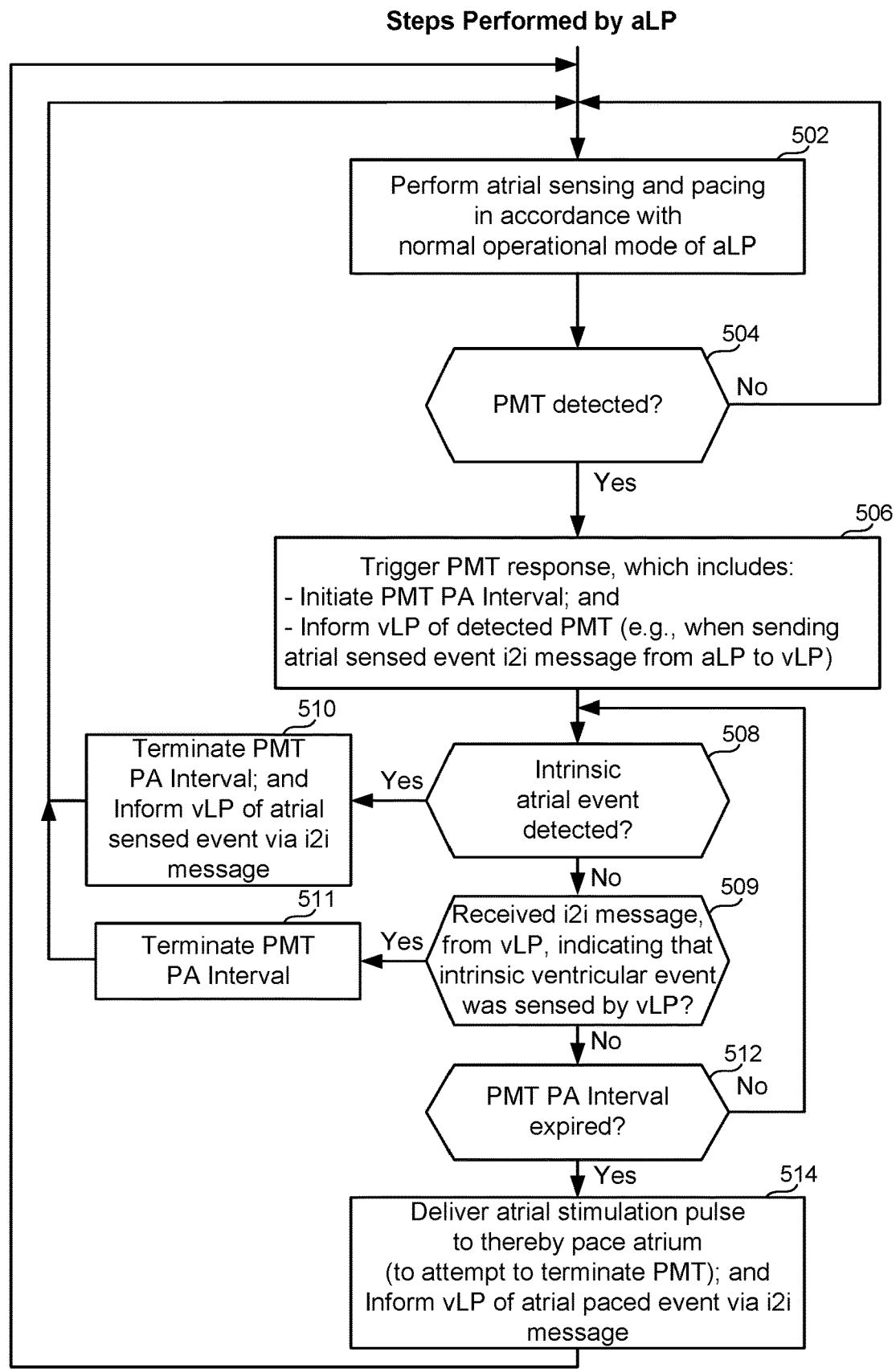
FIGS. 5 and 6 are high level flow diagrams that is used to summarize, respectively, steps that can be performed by an atrial leadless pacemaker (aLP) and steps that can be performed by a ventricular leadless pacemaker (vLP), in order to terminate a PMT, in accordance with certain embodiments of the present technology.
Figure 6:
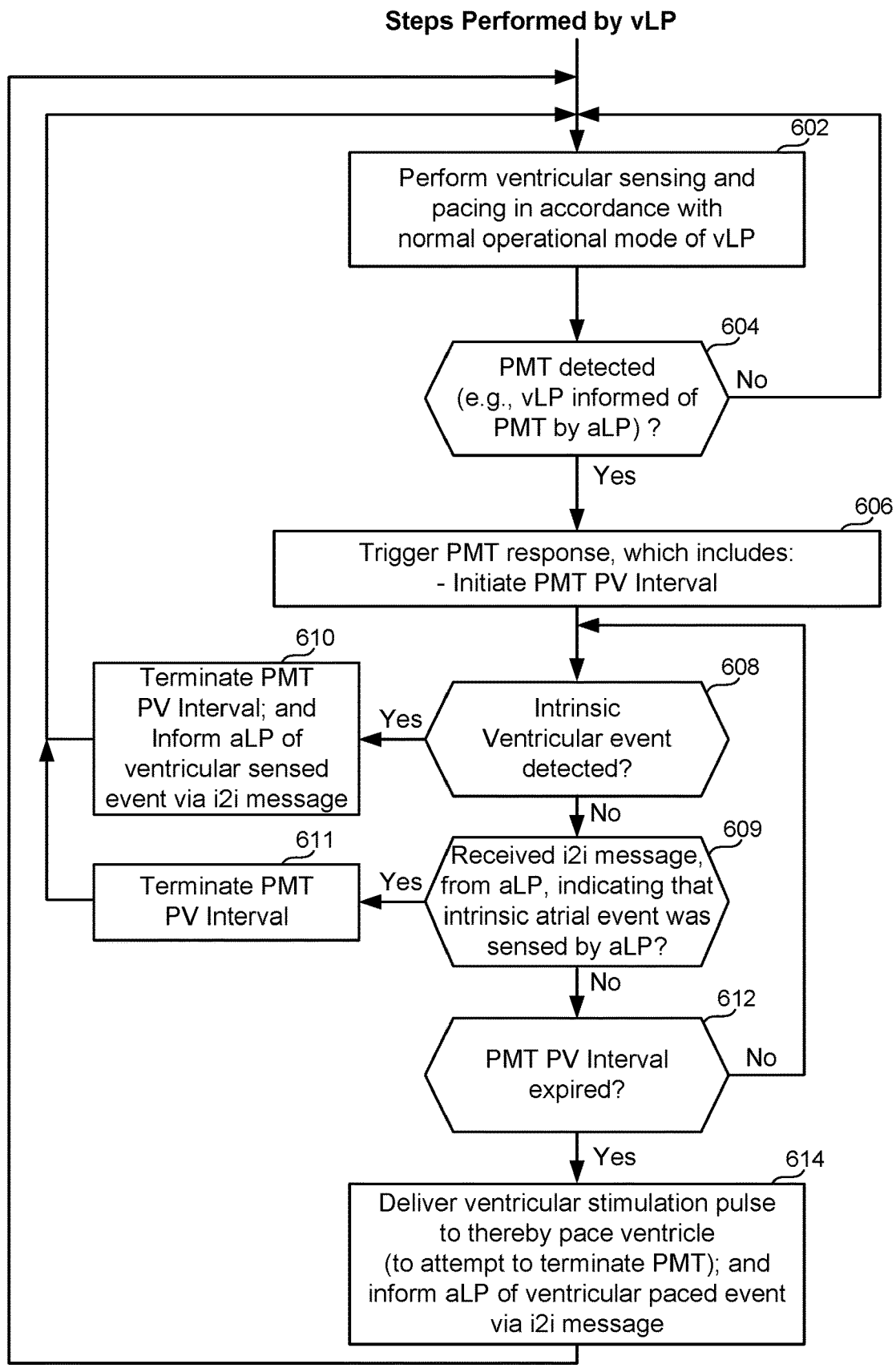

FIGS. 5 and 6 are high level flow diagrams that is used to summarize, respectively, steps that can be performed by the aLP 102 and the vLP 104 in order to terminate a PMT, in accordance with certain embodiments of the present technology. More specifically, FIG. 5 summarizes steps performed by the aLP 102, and FIG. 6 summarized steps performed by the vLP 104.

Referring to FIG. 5, step 502 involves the aLP 102 performing atrial sensing and pacing in accordance with the normal operational mode of the aLP. For example, this may involve that aLP 102 sensing for intrinsic atrial events in the RA, and pacing the RA if a PA interval or AA interval expires without an intrinsic atrial event being detected during the PA interval or AA interval. In the terms "PA interval" and "AA interval", the "P" refers to an intrinsic atrial sensed event (which is also known as a P-wave), and the "A" refers to a paced atrial event (caused by delivery of an A-pulse).

At step 504 there is a determination of whether a PMT is detected. If the answer to the determination as step 504 is No, i.e., if a PMT has not been detected, then flow returns to step 502. In this manner, the aLP 102 performs its atrial sensing and pacing in accordance with its normal operational mode so long as a PMT is not detected.

Still referring to FIG. 5, if the answer to the determination at step 504 is Yes, i.e., if a PMT is detected, then flow goes to step 506. The aLP 102 can detect the PMT itself. Alternatively, the vLP 104 can detect the PMT and send an i2i message to the aLP 102 that informs the aLP 102 of the PMT. Where the aLP 102 detects the PMT itself, the aLP can send an i2i message to the vLP 104 that informs the vLP 104 of the PMT. Various different techniques can be used by the aLP 102 and/or the vLP 104 to detect a PMT. Examples of some PMT detection techniques are provided below. However, it is noted that embodiments of the present technology described herein are not limited to any specific ways of detecting a PMT, since the focus of such embodiments are not related to how a PMT is detected, but rather, are focused on how a PMT is terminated.

As just noted above, if a PMT is detected, then flow goes from step 504 to step 506. At step 506 a PMT response of the aLP 102 is triggered. In accordance with certain embodiments, the PMT response can involve initiating a PMT PA interval that is shorter than the PA interval that the aLP would otherwise use for atrial pacing if a PMT was not detected. Where the PA interval that the aLP 102 would normally use for atrial pacing (if a PMT was not detected) is, e.g., 800 milliseconds (ms), then this means that an atrial pacing pulse (aka an A-pulse) will be delivered 800 ms after an intrinsic atrial sensed event (aka a P-wave), if the PA interval expires without an intrinsic atrial event being detected during the PMT interval. This would provide for a heart rate (HR) of 75 beats per minute (bpm), since 60,000 ms per minute divided by 800 ms per beat equals 75. An exemplary range for the PA interval is from 600 to 1000 ms, which corresponds to a heart rate from 100 to 60 bpm. Lower and/or higher PA intervals are also possible, e.g., another exemplary range for the PA interval is from 400 to 2000 ms, which corresponds to a heart rate of 150 to 30 bmp.

As just explained above, the PMT PA interval (which is initiated in response to a PMT being detected) is shorter than the PA interval that the aLP would otherwise use for atrial pacing if a PMT was not detected. For example, the PMT PA interval can be 330 ms. An exemplary range for the PMT PA interval is from 250 ms to 399 ms, but is not limited thereto. The PMT PA interval can be a programmed value, or can be equal to the PA interval (that the aLP would otherwise use for atrial pacing if a PMT was not detected) minus a programmed value, or can be a specified percentage (e.g., 40%) of the of the PA interval (that the aLP would otherwise use for atrial pacing if a PMT was not detected), but is not limited thereto. Initiating the PMT PA interval can involve initiating a respective timer, which can be its own timer (i.e., a PMT PA interval timer), or the same timer that is normally used for the PA interval can also be used for the PMT PA interval, depending upon the specific implementation.

Assuming that it is the aLP 102 that detected the PMT, the triggered PMT response at step 506 can also involve the aLP 102 informing the vLP 104, via an i2i communication, of the detected PMT. For example, when the aLP 102 sends an i2i communication to the vLP 104, to inform the vLP 104 of an atrial sensed event, the same i2i communication, or a following i2i communication, can inform the vLP 104 of the PMT detected by the aLP 102.

At step 508 there is a determination of whether an intrinsic atrial event is detected. If the answer to the determination at step 508 is No, then flow goes to step 509. At step 509 there is a determination of whether an i2i message was received from the vLP 104 indicating that an intrinsic ventricular event was sensed by the vLP, which is indicative of the PMT having terminated. If the answer to the determination at step 509 is No, then flow goes to step 512. At step 512 there is a determination of whether the PMT PA interval expired. If the answer to the determination at step 512 is No, then flow returns to step 508.

If the answer to the determination at step 508 is Yes (i.e., if an intrinsic atrial event is detected during the PMT PT interval), this is indicative of the PMT being terminated, and flow goes to step 510. At step 510 the PMT PA interval is terminated, and the aLP 102 informs the vLP 104, via an i2i communication, of the intrinsic atrial event that was detected by the aLP 102. Flow then returns to step 502. If the answer to the determination at step 509 is Yes, which is also indicative of the PMT having terminated, then the PMT PA interval is terminated at step 511, and flow returns to step 502.

Returning to the discussion of step 512, if the answer to step 512 is Yes (i.e., if the PMT PA interval expires, without an intrinsic atrial event being detected during the PMT PA interval), then flow goes to step 514. At step 514 an atrial stimulation pulse (aka an A-pulse) is delivered to the atrium to thereby pace that atrium, to attempt to terminate the PMT. Additionally, the aLP 102 informs the vLP 104, via an i2i communication, of the atrial paced event. For example, when the aLP 102 sends an i2i communication to the vLP 104, to inform the vLP 104 of an atrial paced event, the same i2i communication, or a following i2i communication, can inform the vLP 104 of the atrial paced event caused by the aLP 102. Flow then returns to step 502, as shown in FIG. 5. If the PMT was successfully terminated, then the next time step 504 is performed the answer to the determination at step 504 should be No. However, if the PMT was not successfully terminated, then the next time step 504 is performed the answer to the determination at step 504 should again be Yes and flow will again go to step 506 to trigger another PMT response.

Referring now to FIG. 6, step 602 involves the vLP 104 performing ventricular sensing and pacing in accordance with the normal operational mode of the vLP. For example, this may involve that vLP 104 sensing for intrinsic ventricular events in the RV, and pacing the RV if a RV interval or VV interval expires without an intrinsic ventricular event being detected during the RV or VV interval. In the terms "RV interval" and "VV interval", the "R" refers to an intrinsic ventricular sensed event (which is also known as an R-wave), and the "V" refers to a paced ventricular event (caused by delivery of a V-pulse).

At step 604 there is a determination of whether a PMT is detected. If the answer to the determination as step 604 is No, i.e., if a PMT has not been detected, then flow returns to step 602. In this manner, the vLP 104 performs its ventricular sensing and pacing in accordance with its normal operational mode so long as a PMT is not detected.

Still referring to FIG. 6, if the answer to the determination at step 604 is Yes, i.e., if a PMT is detected, then flow goes to step 606. Depending upon implementation, the vLP 104 can detect the PMT itself. Alternatively, the aLP 102 can detect the PMT and send an i2i message to the vLP 104 that informs the vLP 104 of the PMT. Where the vLP 104 detects the PMT itself, the vLP 104 can send an i2i message to the aLP 102 that informs the aLP 102 of the PMT. As noted above, various different techniques can be used by the aLP 102 and/or the vLP 104 to detect a PMT, some examples of which are provided below.

As just noted above, if a PMT is detected, then flow goes from step 604 to step 606. At step 606 a PMT response of the vLP 104 is triggered. In accordance with certain embodiments, the PMT response can involve initiating a PMT PV interval. In accordance with certain embodiments, the PMT PV interval equals the PMT PA interval (discussed above with reference to step 506 in FIG. 5) plus a delay, wherein the delay can be either a fixed value (e.g., 30 ms) or a rate dependent value (e.g., within the range of 10 ms to 50 ms). The PMT PV interval is made longer than the PMT PA interval to provide a safety margin to ensure that the PMT PV interval does not expire prior to the PMT PA interval expiring, while taking into account that it takes some time for the aLP to inform the vLP of the detected PMT via an i2i communication (or vice versa, for the vLP to inform the aLP of the detected PMT via an i2i communication) and that it takes some time for the LP that receive the i2i communication (informing it of the detected PMT), to demodulate the i2i communication, and to trigger its PMT response. Initiating the PMT PV interval can involve initiating a respective timer, which can be its own timer (i.e., a PMT PV interval timer), or the same timer that is normally used for the PV interval can also be used for the PMT PV interval, depending upon the specific implementation.

At step 608 there is a determination of whether an intrinsic ventricular event is detected. If the answer to the determination at step 608 is No, then flow goes to step 609. At step 609 there is a determination of whether an i2i message was received from the aLP 102 indicating that an intrinsic atrial event was sensed by the aLP, which is indicative of the PMT being terminated. If the answer to the determination at step 609 is No, then flow goes to step 612. At step 612 there is a determination of whether the PMT PV interval expired. If the answer to the determination at step 612 is No, then flow returns to step 608.

If the answer to the determination at step 608 is Yes (i.e., if an intrinsic ventricular event is detected during the PMT PV interval), this is indicative of the PMT being terminated, and flow goes to step 610. At step 610 the PMT PV interval is terminated, and the vLP 104 informs the aLP 102, via an i2i communication, of the intrinsic ventricular event that was detected by the vLP 104. Flow then returns to step 602. If the answer to the determination at step 609 is Yes, which is also indicative of the PMT being terminated, then the PMT PV interval is terminated at step 611, and flow returns to step 602.

Returning to step 612, if the answer to the determination at step 612 is Yes (i.e., if the PMT PV interval expires, without an intrinsic ventricular event being detected during the PMT PV interval), then flow goes to step 614. At step 614 a ventricular stimulation pulse (aka a V-pulse) is delivered to the ventricle to thereby pace that ventricle, to attempt to terminate the PMT. Additionally, the vLP 104 informs the aLP 102, via an i2i communication, of the ventricular paced event. Flow then returns to step 602, as shown in FIG. 6.

As noted above, there are various different ways that an LP can detect a PMT. For example, an LP can detect a PMT if for a specified number (e.g., 10) of consecutive cardiac cycles, an atrial sensed event (AS) is followed by a ventricular paced event (AP) and the pacing rate is greater than a specified rate (e.g., 130 bpm). For another example, a PMT can be detected by monitoring VP interval stability for a specific number (e.g., 10) of consecutive cardiac cycles, wherein a VP interval is the time from a ventricular paced event (a V-pulse) to in intrinsic atrial sensed event (a P-wave). More specifically, if it is determined that the VP interval is stable (e.g., within a specified tolerance) for a specific number of (e.g., 10) consecutive cardiac cycles, the next PV interval is purposely varied (increased or decreased by a known amount, e.g., 50 ms). If the VP interval on the next cardiac cycle remains substantially the same as it was in the VP intervals measured during the previous consecutive cardiac cycles having the stable VP interval, then the P-wave is likely caused by retrograde conduction and a PMT is detected. However, if the VP interval on the next cardiac cycle changes (decreases or increases) by the amount of the purposeful variation (e.g., 50 ms), then the P-wave is likely not caused by retrograde conduction and a PMT is not detected. These are just a few examples of how an LP can detect a PMT, which are not intended to be limiting. Other variations are also possible.

Figure 7:
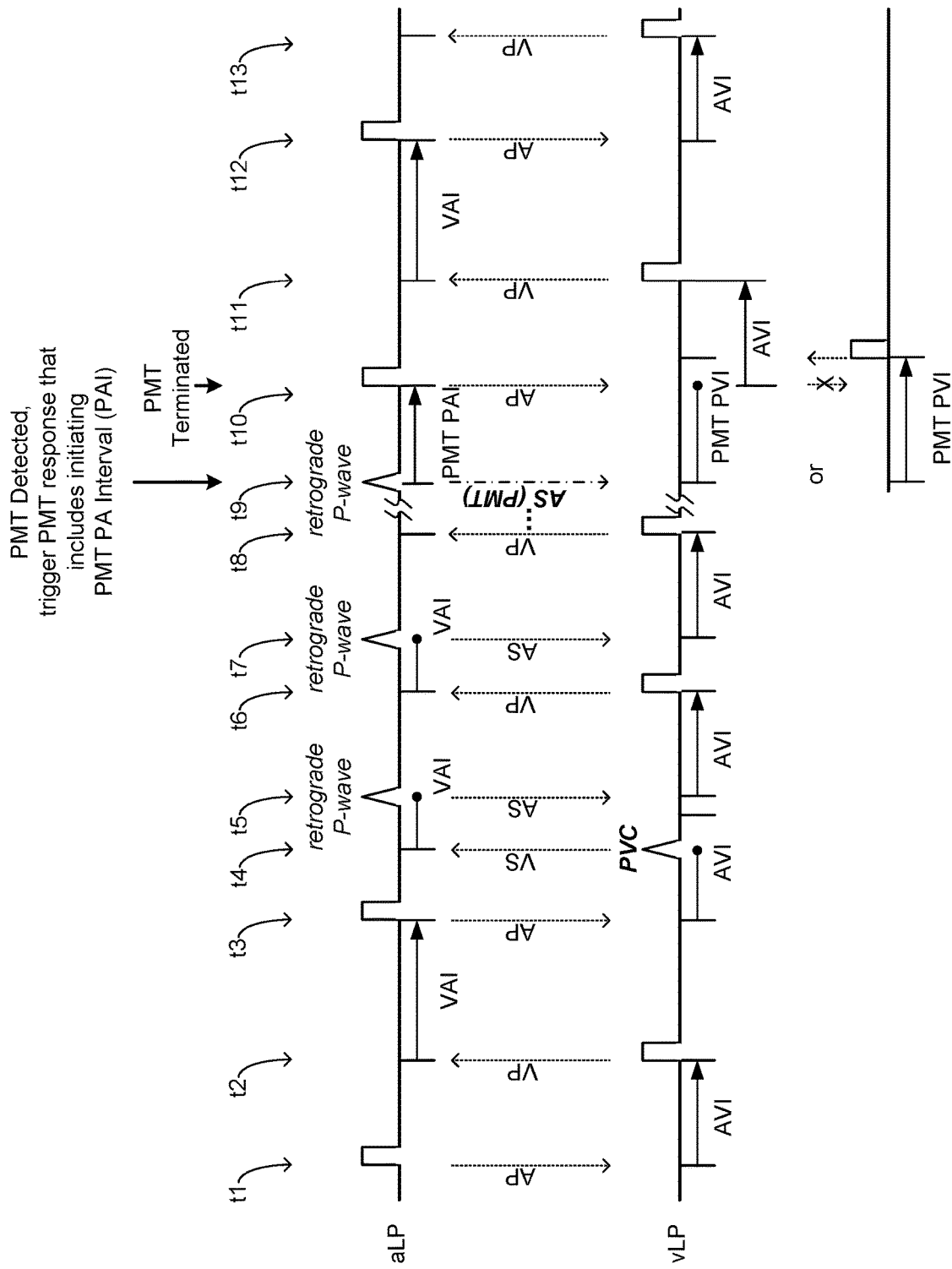
FIGS. 7, 8 and 9 are timing diagrams illustrating operations of an aLP and a vLP in communication with one another in manners that can be used to terminate a PMT in accordance with various embodiments of the present technology.
Figure 8:
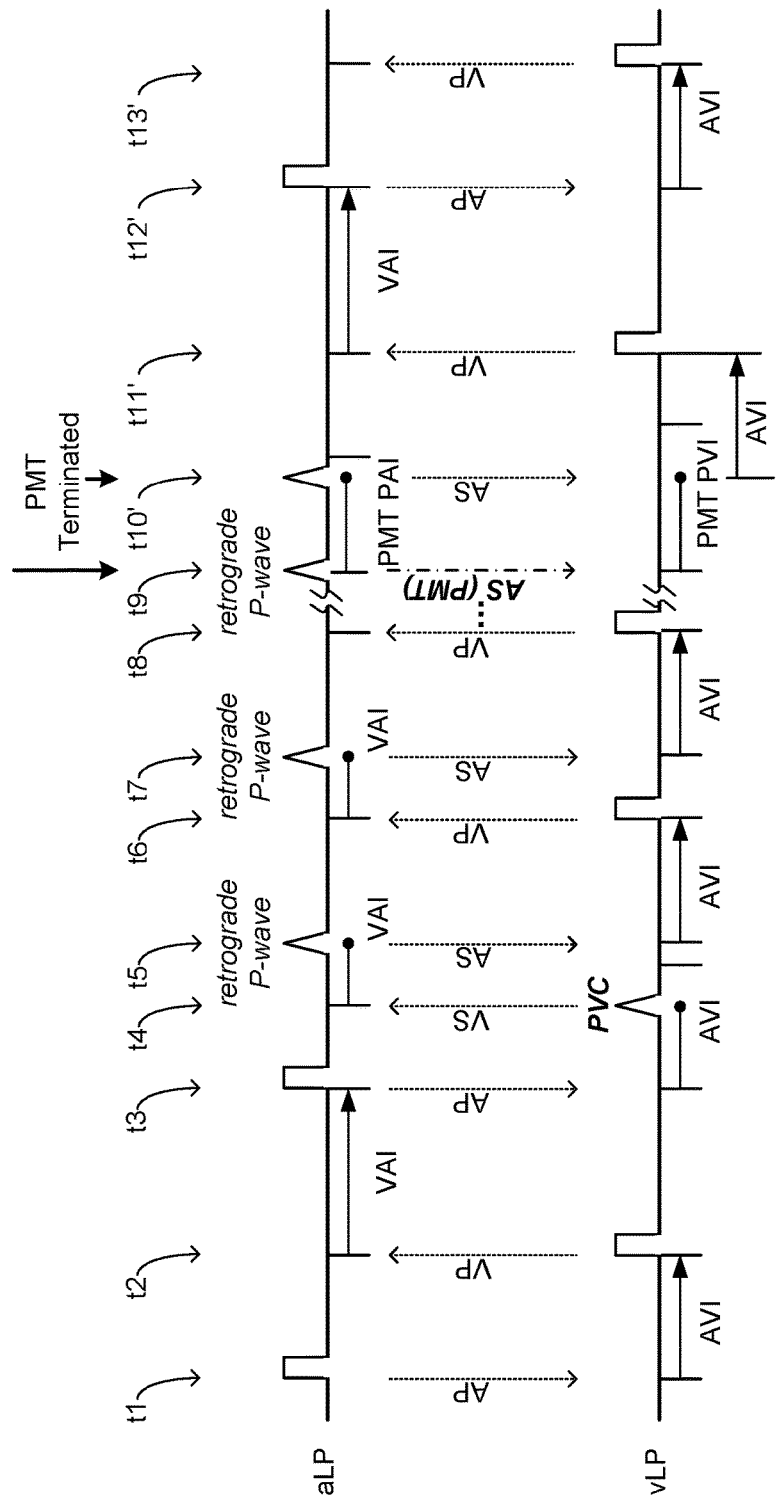
Figure 9:
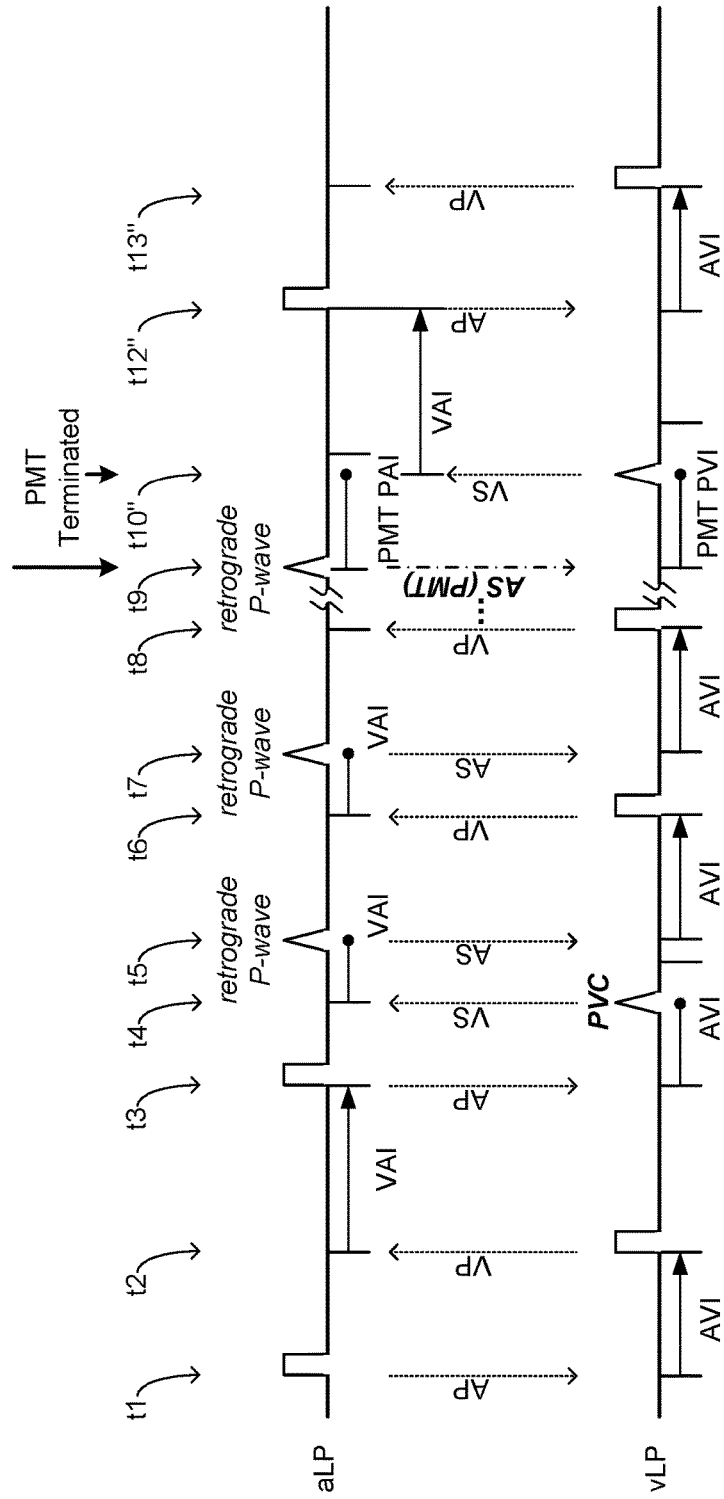

Reference is now made to FIGS. 7, 8 and 9, which are timing diagrams illustrating operations of the aLP 102 and vLP 104, and i2i communications therebetween, in manners that can be used to terminate a PMT in accordance with various embodiments of the present technology. In each of these figures, the upper time line is indicative of paced atrial events caused by the aLP 102 and intrinsic atrial events sensed by the aLP 102, and the lower time line is indicative of paced ventricular events caused by the vLP 104 and intrinsic ventricular events caused by the vLP 104. The dotted arrows between the upper and lower time lines is indicative of i2i messages sent between the aLP 102 and the vLP 104, with the arrow indicative of the direction of the i2i message.

Referring to FIG. 7, at time t1 the aLP 102 causes a paced atrial event (aka an atrial paced event, or an AP), and sends an i2i message to the vLP 104 to inform the vLP of the AP. The vLP 104, in response to being informed of the AP, initiates an atrioventricular (AV) interval (aka AVI).

At time t2 the AV interval (aka AVI) expires and the vLP 104 causes a paced ventricular event (aka a ventricular paced event, or a VP), and the vLP 104 sends an i2i message to the aLP 102 to inform the aLP 102 of the VP. The aLP, in response to being informed of the VP, initiates a VA interval (aka VAI).

At time t3, the VA interval (aka VAI) expires and the aLP 102 causes an AP, and sends an i2i message to the vLP 104 to inform the vLP of the AP. The vLP 104, in response to being informed of the AP, initiates an AVI.

At time t4 a premature ventricular contraction (PVC) occurs, which cause the vLP 104 to terminate the AVI and send an i2i message to the aLP 102 to inform the aLP 102 of the VS (which in this case is a PVC). The aLP 102, in response to being informed of the VS, initiates a VAI.

At time t5 a retrograde P-wave is shown as occurring. The retrograde P-wave is detected by the aLP 102 as an atrial sensed event (AS), in response to which the aLP 102 terminates the VAI, and sends an i2i message to the vLP 104 to inform the vLP of the AS. The vLP 104, in response to being informed of the AS, initiates an AVI.

At time t6, the AVI interval expires and the vLP 104 causes a VP, and the vLP 104 sends an i2i message to the aLP 102 to inform the aLP 102 of the VP. The aLP, in response to being informed of the VP, initiates a VAI.

At time t7 another retrograde P-wave is shown as occurring. The retrograde P-wave is detected by the aLP 102 as an AS, in response to which the aLP 102 terminates the VAI, and sends an i2i message to the vLP 104 to inform the vLP of the AS. The vLP 104, in response to being informed of the AS, initiates an AVI.

At time t8, the AVI interval expires and the vLP 104 causes a VP, and the vLP 104 sends an i2i message to the aLP 102 to inform the aLP 102 of the VP. The aLP, in response to being informed of the VP, initiates another VAI.

While not specifically shown in the timing diagram of FIGS. 7-9 (into order to minimize clutter in the timing diagrams), the aLP will initiate a normal PA interval (aka PAI) whenever the aLP 102 detects an AS (which may or may not be a retrograde P-wave type AS), assuming a PMT has not yet been detected.

It is presumed that between times t8 and t9 additional retrograde P-waves occur (which are not shown), eventually resulting in the aLP 102 detecting a PMT, and triggering a PMT response, at time t9.

In response to the aLP 102 detecting the PMT at time t9, the aLP 102 initiates a PMT PA interval that is shorter than the PA interval (aka the normal PA interval) that the aLP uses for atrial pacing when a PMT is not detected. Additionally, the aLP 102 sends an i2i message(s) to the vLP 104 to inform the vLP 104 of the AS and the PMT. The vLP 104, in response to being informed of the PMT, initiates a PMT PV interval (aka PMT PVI), that is longer than the PMT PA interval.

Still referring to FIG. 7, at time t10, the PMT PAI is shown as expiring, in response to which the aLP 102 causes an AP, and the aLP 102 informs the vLP 104, via an i2i message, of the AP. At this point it is presumed that the PMT has been terminated. The vLP 104, in response to being informed of the AP, terminates that PMT PVI and initiates a normal AVI. At time t11, the AVI expires, in response to which the vLP 104 causes a VP, and the vLP 104 informs the aLP 102, via an i2i message, of the VP. The aLP 102, in response to being informed of the VP, initiates a VAI.

Normal operation of the aLP 102 and the vLP 104 then occurs at times t12 and t13. In this example, at time t12 that VAI expires, in response to which the aLP 102 causes an AP and informs the vLP 104 of the AP. The vLP 104, in response to being informed of the AP, initiates an AVI. At time t13 the AVI expires, in response to which the vLP 104 causes a VP and informs the aLP 102 of the VP, in response to which the aLP 102 initiates another AVI, etc. It is noted that instead of the VAI interval expiring at time t12, an AS event could have been sensed between time t11 and t12, and the LPs would respond accordingly in accordance with their normal operation since the PMT had been terminated.

If the vLP 104 fails to successfully receive the i2i communication from the aLP 102, which was sent at time t10, then the PMT PVI interval will eventually expire (between times t10 and t11) and the vLP 104 will cause a VP at that point, as shown in the lower right corner in FIG. 7. This will have no adverse effect on the patient, and the PMT should still be terminated.

In the example of FIG. 7, the aLP 102, in response to the PMT PA interval expiring without an intrinsic atrial event being detected during the PMT PA interval, paces the atrial cardiac chamber at time t10, and informs the vLP, via an i2i communication, of pacing the atrial cardiac chamber.

In the example of FIG. 8, an intrinsic atrial event (aka an AS) is instead detected by the aLP 102 during the PMT PA interval, as shown in time t10' (which would occur earlier than time t10 shown in FIG. 7). Everything prior to time t10' in FIG. 8 is the same as it was in FIG. 7, and thus need not be described again. In response to the aLP 102 detecting the AS at time t10', the aLP 102 informs the vLP 104, via an i2i communication, of the AS. At this point it is presumed that the PMT has terminated. The vLP 104, in response to being informed of the AS, terminates the PMT PVI and initiates a normal AVI. At time t11', the AVI expires, in response to which the vLP 104 causes a VP, and the vLP 104 informs the aLP 102, via an i2i message, of the VP. The aLP 102, in response to being informed of the VP, initiates a VAI. Normal operation of the aLP 102 and the vLP 104 then occurs at times t12' and t13'.

In the example of FIG. 9, the vLP 104 detects an intrinsic ventricular event (aka a VS) during the PMT PV interval, as shown at time t10", in response to which the vLP 104 terminates the PMT PV interval. Everything prior to time t10" in FIG. 9 is the same as it was in FIG. 7, and thus need not be described again. In response to the vLP 104 detecting the VS at time t10", the vLP 104 informs the aLP 102, via an i2i communication, of the VS. At this point it is presumed that the PMT has terminated. The aLP 102, in response to being informed of the VP, initiates a VAI. Normal operation of the aLP 102 and the vLP 104 then occurs at times t12" and t13".

Figure 10:
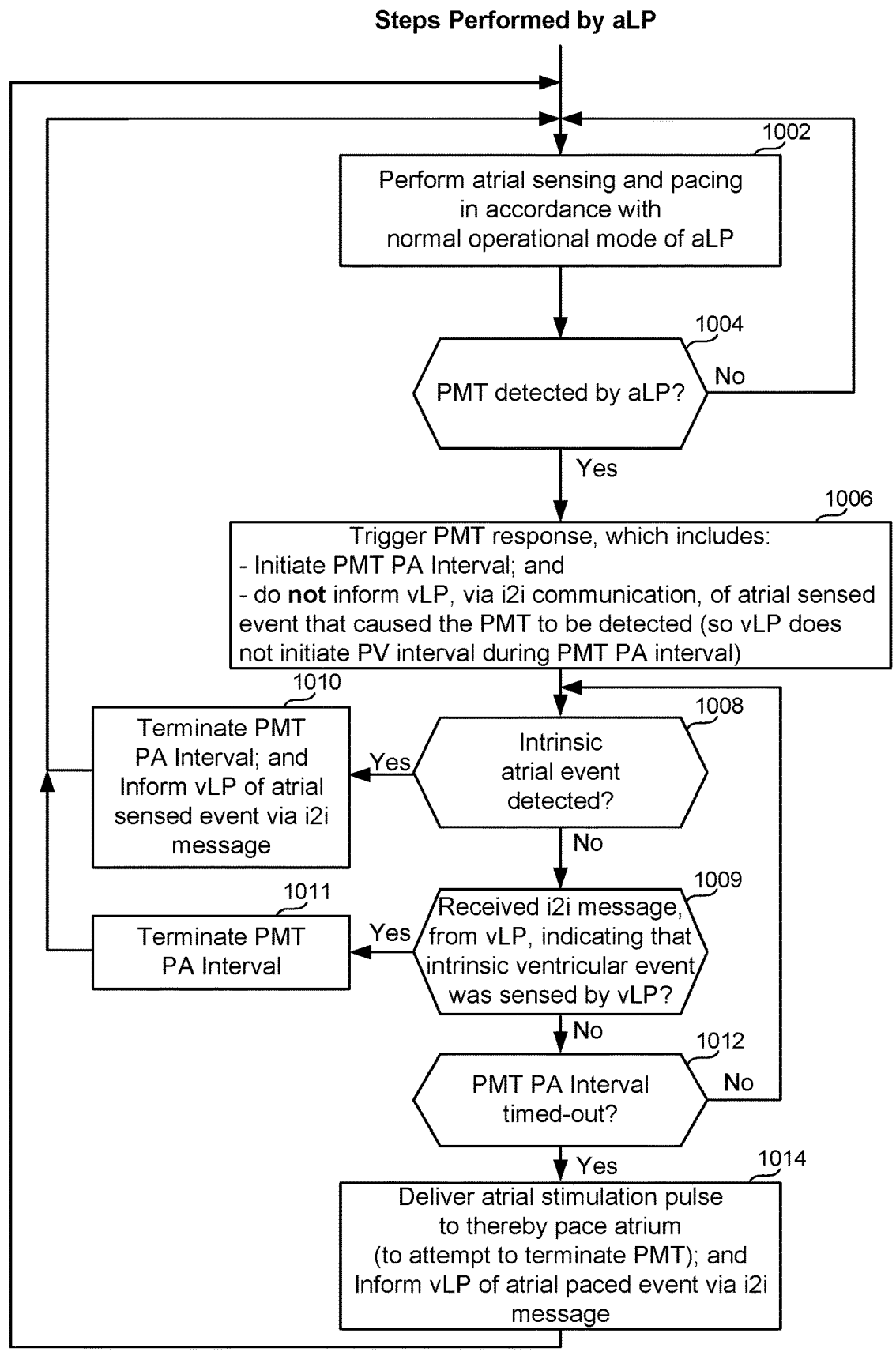
FIG. 10 high level flow diagrams that is used to summarize steps that can be performed by an aLP in order to terminate a PMT, in accordance with further embodiments of the present technology.

FIG. 10 is high level flow diagrams that is used to summarize steps that can be performed by the aLP 102, in order to terminate a PMT, in accordance with further embodiments of the present technology.

Referring to FIG. 10, step 1002 involves the aLP 102 performing atrial sensing and pacing in accordance with the normal operational mode of the aLP. Examples of this were discussed above with reference to step 502 with reference to FIG. 5.

At step 1004 there is a determination of whether a PMT is detected by the aLP 102. As noted above, embodiments of the present technology described herein are not limited to any specific ways of detecting a PMT, since the focus of such embodiments are not related to how a PMT is detected, but rather, are focused on how a PMT is terminated.

If the answer to the determination as step 1004 is No, i.e., if a PMT has not been detected, then flow returns to step 1002. In this manner, the aLP 102 performs its atrial sensing and pacing in accordance with its normal operational mode so long as a PMT is not detected.

If the answer to the determination at step 1004 is Yes, i.e., if a PMT is detected, then flow goes to step 1006. At step 1006 a PMT response of the aLP 102 is triggered. In accordance with this embodiment, the PMT response involves initiating a PMT PA interval that is shorter than the PA interval that the aLP would otherwise use for atrial pacing if a PMT was not detected, as was also the case in the embodiment described above with reference to FIG. 5. Exemplary values for the PA interval and the PMT PA interval were discussed above with reference to step 506 of FIG. 5. In contrast to the embodiment described with reference to FIG. 5, in this embodiment, the PMT response also involves the aLP 102 not informing the vLP 104, via an i2i communication, of the atrial sensed event that caused the aLP 102 to detect the PMT. In other words, part of the PMT response involves the aLP 102 abstaining from informing the vLP 104 of an intrinsic atrial event sensed by the aLP 102. This will have the effect of the vLP 104 not initiating a PVT interval during the PMT PA interval, which should break the reentrant circuit and thereby terminate the PMT.

At step 1008 there is a determination of whether an intrinsic atrial event is detected. If the answer to the determination at step 1008 is No, then flow goes to step 1009. At step 1009 there is a determination of whether an i2i message was received from the vLP 104 indicating that an intrinsic ventricular event was sensed by the vLP, which is indicative of the PMT having terminated. If the answer to the determination at step 1009 is No, then flow goes to step 1012. At step 1012 there is a determination of whether the PMT PA interval expired. If the answer to the determination at step 1012 is No, then flow returns to step 1008.

If the answer to the determination at step 1008 is Yes (i.e., if an intrinsic atrial event is detected during the PMT PT interval), this is indicative of the PMT being terminated, and flow goes to step 1010. At step 1010 the PMT PA interval is terminated, and the aLP 102 informs the vLP 104, via an i2i communication, of the intrinsic atrial event that was detected by the aLP 102. Flow then returns to step 1002. If the answer to the determination at step 1009 is Yes, which is also indicative of the PMT having terminated, then the PMT PA interval is terminated at step 1011, and flow returns to step 1002.

Returning to the discussion of step 1012, if the answer to step 1012 is Yes (i.e., if the PMT PA interval expires, without an intrinsic atrial event being detected during the PMT PA interval), then flow goes to step 1014. At step 1014 an atrial stimulation pulse (aka an A-pulse) is delivered to the atrium to thereby pace that atrium, to attempt to terminate the PMT. Additionally, the aLP 102 informs the vLP 104, via an i2i communication, of the atrial paced event. For example, when the aLP 102 sends an i2i communication to the vLP 104, to inform the vLP 104 of an atrial paced event, the same i2i communication, or a following i2i communication, can inform the vLP 104 of the atrial paced event caused by the aLP 102. Flow then returns to step 1002, as shown in FIG. 10. If the PMT was successfully terminated, then the next time step 1004 is performed the answer to the determination at step 1004 should be No. However, if the PMT was not successfully terminated, then the next time step 1004 is performed the answer to the determination at step 1004 should again be Yes and flow will again go to step 1006 to trigger another PMT response.

Figure 11:
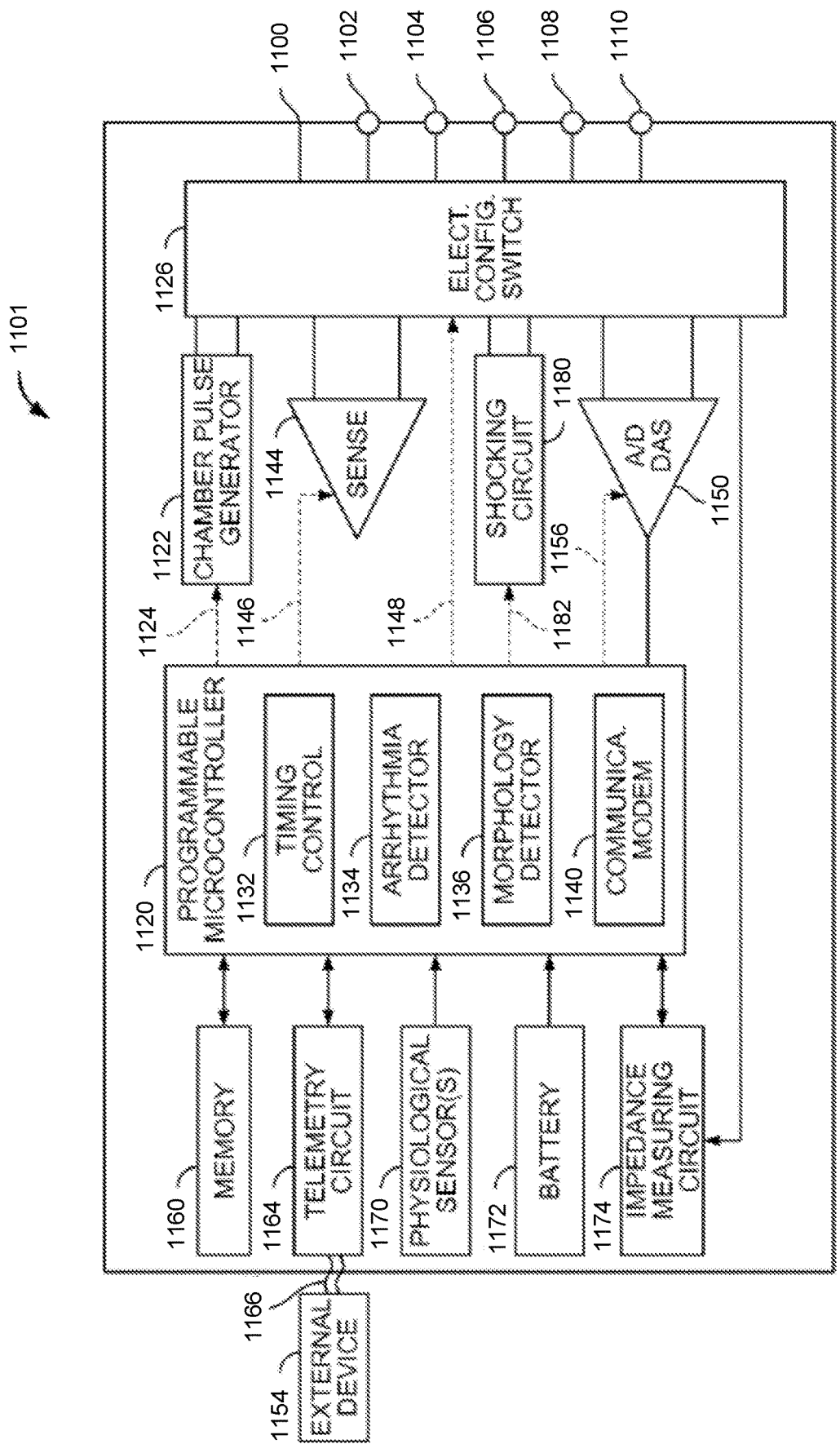
FIG. 11 shows a block diagram of one embodiment of an LP that is implanted into a patient as part of an implantable cardiac system in accordance with certain embodiments herein.

FIG. 11 shows a block diagram of one embodiment of an LP 1101 (e.g., the aLP 102 or the vLP 104) that is implanted into the patient as part of the implantable cardiac system in accordance with certain embodiments herein. LP 1101 may be implemented as a full-function biventricular pacemaker, equipped with both atrial and ventricular sensing and pacing circuitry for four chamber sensing and stimulation therapy (including both pacing and shock treatment). Optionally, LP 1101 may provide full-function cardiac resynchronization therapy. Alternatively, LP 1101 may be implemented with a reduced set of functions and components. For instance, the IMD may be implemented without ventricular sensing and pacing.

LP 1101 has a housing 1100 to hold the electronic/computing components. Housing 1100 (which is often referred to as the "can", "case", "encasing", or "case electrode") may be programmably selected to act as the return electrode for certain stimulus modes. Housing 1100 may further include a connector (not shown) with a plurality of terminals 1102, 1104, 1106, 1108, and 1110. The terminals may be connected to electrodes that are located in various locations on housing 1100 or elsewhere within and about the heart. LP 1101 includes a programmable microcontroller 1120 that controls various operations of LP 1101, including cardiac monitoring and stimulation therapy. Microcontroller 1120 includes a microprocessor (or equivalent control circuitry), RAM and/or ROM memory, logic and timing circuitry, state machine circuitry, and I/O circuitry.

LP 1101 further includes a pulse generator 1122 that generates stimulation pulses and communication pulses for delivery by one or more electrodes coupled thereto. Pulse generator 1122 is controlled by microcontroller 1120 via control signal 1124. Pulse generator 1122 may be coupled to the select electrode(s) via an electrode configuration switch 1126, which includes multiple switches for connecting the desired electrodes to the appropriate I/O circuits, thereby facilitating electrode programmability. Switch 1126 is controlled by a control signal 1128 from microcontroller 1120.

In the embodiment of FIG. 11, a single pulse generator 1122 is illustrated. Optionally, the IMD may include multiple pulse generators, similar to pulse generator 1122, where each pulse generator is coupled to one or more electrodes and controlled by microcontroller 1120 to deliver select stimulus pulse(s) to the corresponding one or more electrodes.

Microcontroller 1120 is illustrated as including timing control circuitry 1132 to control the timing of the stimulation pulses (e.g., pacing rate, atrio-ventricular (AV) delay, atrial interconduction (A-A) delay, or ventricular interconduction (V-V) delay, etc.). The aforementioned delays can also be referred to as intervals, e.g., an AV delay can also be referred to as an AV interval, aka the AVI. Timing control circuitry 1132 may also be used for the timing of refractory periods, blanking intervals, noise detection windows, evoked response windows, alert intervals, marker channel timing, and so on. The timing control circuitry 1132 can also control the timing of various other intervals discussed above, such as, but not limited to, a PA interval, a PMT PA interval, VA interval, PMT PV interval, and/or the like. Timing control circuitry 1132 can include a respective timer for each interval being tracked, or a same timer may be used to track more than one interval, depending upon implementation. Where the timing control circuitry 1132 includes multiple timers, the multiple timers can all have the same timing resolution, or different timers can have different timing resolutions, e.g., one or more timers can have a timing resolution of ~1 ms, and one or more other times can have a timing resolution of ~8 ms, but are not limited thereto.

Microcontroller 1120 also has an arrhythmia detector 1134 for detecting arrhythmia conditions and a morphology detector 1136. Although not shown, the microcontroller 1120 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

LP 1101 is further equipped with a communication modem (modulator/demodulator) 1140 to enable wireless communication with the remote slave pacing unit. Modem 1140 may include one or more transmitters and two or more receivers as discussed herein in connection with FIG. 1B. In one implementation, modem 1140 may use low or high frequency modulation. As one example, modem 1140 may transmit i2i messages and other signals through conductive communication between a pair of electrodes. Modem 1140 may be implemented in hardware as part of microcontroller 1120, or as software/firmware instructions programmed into and executed by microcontroller 1120. Alternatively, modem 1140 may reside separately from the microcontroller as a standalone component.

LP 1101 includes a sensing circuit 1144 selectively coupled to one or more electrodes, that perform sensing operations, through switch 1126 to detect the presence of cardiac activity in the right chambers of the heart. Sensing circuit 1144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1126 determines the sensing polarity of the cardiac signal by selectively closing the appropriate switches. In this way, the clinician may program the sensing polarity independent of the stimulation polarity.

The output of sensing circuit 1144 is connected to microcontroller 1120 which, in turn, triggers or inhibits the pulse generator 1122 in response to the presence or absence of cardiac activity. Sensing circuit 1144 receives a control signal 1146 from microcontroller 1120 for purposes of controlling the gain, threshold, polarization charge removal circuitry (not shown), and the timing of any blocking circuitry (not shown) coupled to the inputs of the sensing circuitry.

In the embodiment of FIG. 11, a single sensing circuit 1144 is illustrated. Optionally, the IMD may include multiple sensing circuits, similar to sensing circuit 1144, where each sensing circuit is coupled to one or more electrodes and controlled by microcontroller 1120 to sense electrical activity detected at the corresponding one or more electrodes. Sensing circuit 1144 may operate in a unipolar sensing configuration or in a bipolar sensing configuration.

LP 1101 further includes an analog-to-digital (A/D) data acquisition system (DAS) 1150 coupled to one or more electrodes via switch 1126 to sample cardiac signals across any pair of desired electrodes. Data acquisition system 1150 is configured to acquire intracardiac electrogram signals, convert the raw analog data into digital data, and store the digital data for later processing and/or telemetric transmission to an external device 1154 (e.g., a programmer, local transceiver, or a diagnostic system analyzer). Data acquisition system 1150 is controlled by a control signal 1156 from the microcontroller 1120.

Microcontroller 1120 is coupled to a memory 1160 by a suitable data/address bus. The programmable operating parameters used by microcontroller 1120 are stored in memory 1160 and used to customize the operation of LP 1101 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 1101 may be non-invasively programmed into memory 1160 through a telemetry circuit 1164 in telemetric communication via communication link 1166 with external device 1154. Telemetry circuit 1164 allows intracardiac electrograms and status information relating to the operation of LP 1101 (as contained in microcontroller 1120 or memory 1160) to be sent to external device 1154 through communication link 1166.

LP 1101 can further include magnet detection circuitry (not shown), coupled to microcontroller 1120, to detect when a magnet is placed over the unit. A magnet may be used by a clinician to perform various test functions of LP 1101 and/or to signal microcontroller 1120 that external device 1154 is in place to receive or transmit data to microcontroller 1120 through telemetry circuits 1164.

LP 1101 can further include one or more physiological sensors 1170. Such sensors are commonly referred to as "rate-responsive" sensors because they are typically used to adjust pacing stimulation rates according to the exercise state of the patient. However, physiological sensor 1170 may further be used to detect changes in cardiac output, changes in the physiological condition of the heart, or diurnal changes in activity (e.g., detecting sleep and wake states). Signals generated by physiological sensors 1170 are passed to microcontroller 1120 for analysis. Microcontroller 1120 responds by adjusting the various pacing parameters (such as rate, AV Delay, V-V Delay, etc.) at which the atrial and ventricular pacing pulses are administered. While shown as being included within LP 1101, physiological sensor(s) 1170 may be external to LP 1101, yet still be implanted within or carried by the patient. Examples of physiologic sensors might include sensors that, for example, sense respiration rate, pH of blood, ventricular gradient, activity, position/posture, minute ventilation (MV), and so forth.

A battery 1172 provides operating power to all of the components in LP 1101. Battery 1172 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1172 also desirably has a predictable discharge characteristic so that elective replacement time can be detected. As one example, LP 1101 employs lithium/silver vanadium oxide batteries.

LP 1101 further includes an impedance measuring circuit 1174, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1174 is coupled to switch 1126 so that any desired electrode may be used. In this embodiment LP 1101 further includes a shocking circuit 1180 coupled to microcontroller 1120 by a data/address bus 1182.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP may need to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or WI), and for the IPG to utilize the proper set of settings and algorithms (e.g., V-AutoCapture vs ACap-Confirm, sensing sensitivities, etc.).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 5, 6 and 10. For another example, it is possible to change the boundaries of some of the dashed blocks shown in FIG. 11.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for terminating a pacemaker mediated tachycardia (PMT), the method for use by an implantable system including an atrial leadless pacemaker (aLP) and a ventricular leadless pacemaker (vLP), the aLP configured to be implanted within or on an atrial cardiac chamber, wherein during a period that the PMT is not detected the aLP is also configured to deliver an atrial pacing pulse to the atrial cardiac chamber in response to a PA interval expiring without an intrinsic atrial event being detected during the PA interval, the vLP configured to be implanted within or on a ventricular cardiac chamber, and the aLP and the vLP capable of performing implant-to-implant (i2i) communication with one another, the method comprising:
  the aLP performing atrial sensing to thereby monitor for intrinsic atrial events in the atrial cardiac chamber;
  the vLP performing ventricular sensing to thereby monitor for intrinsic ventricular events in the ventricular chamber;
  one of the aLP or the vLP detecting the PMT;
  the one of the aLP or the vLP that detected the PMT informing the other one of the aLP or the vLP, via an i2i communication, that the PMT was detected;
  the aLP, in response to the PMT being detected, initiating a PMT PA interval that is shorter than the PA interval that the aLP would otherwise use for atrial pacing if the PMT was not detected; and
  the vLP, in response to the PMT being detected, initiating a PMT PV interval that is longer than the PMT PA interval;
  wherein the PA interval specifies when an atrial pacing pulse should be delivered by the aLP to the atrial cardiac chamber following an intrinsic atrial sensed event, in response to the PA interval expiring without another intrinsic atrial event being detected during the PA interval, during a period that the PMT has not been detected;
  wherein the PMT PA interval specifies when an atrial pacing pulse should be delivered by the aLP to the atrial cardiac chamber following an intrinsic atrial sensed event, in response to the PMT PA interval expiring without another intrinsic atrial event being detected during the PMT PA interval, during a period that the PMT has been detected; and
  wherein the PMT PV interval specifies when a ventricular pacing pulse should be delivered by the vLP to the ventricular cardiac chamber following an intrinsic atrial sensed event, in response to the PMT PV interval expiring without an intrinsic ventricular event being detected during the PMT PV interval, during a period that the PMT has been detected.

2. The method of claim 1, further comprising the aLP detecting the PMT PA interval expiring without an intrinsic atrial event being detected during the PMT PA interval, and in response thereto the aLP:
  pacing the atrial cardiac chamber; and
  informing the vLP, via an i2i communication, of the pacing the atrial cardiac chamber.

3. The method of claim 2, further comprising the vLP receiving the i2i communication from the aLP that informs the vLP of the pacing the atrial cardiac chamber, and in response thereto the vLP:
  terminating the PMT PV interval; and
  initiating an atrioventricular (AV) interval;
  wherein the AV interval specifies when a ventricular pacing pulse should be delivered by the vLP to the ventricular cardiac chamber following a paced atrial event, in response to the AV interval expiring without an intrinsic ventricular event being detected during the AV interval, during a period that the PMT has not been detected; and
  wherein the paced atrial event can be the pacing of the atrial cardiac chamber that the aLP informs the vLP about via the i2i communication.

4. The method of claim 1, further comprising the aLP detecting an intrinsic atrial event during the PMT PA interval, and in response thereto the aLP:
  terminating the PMT PA interval; and
  informing the vLP, via an i2i communication, of the detected intrinsic atrial event.

5. The method of claim 4, further comprising the vLP receiving the i2i communication from the aLP that informs the vLP of the intrinsic atrial event being detected, and in response thereto the vLP:
  terminating the PMT PV interval; and
  initiating a PV interval;
  wherein the PV interval specifies when a ventricular pacing pulse should be delivered by the vLP to the ventricular cardiac chamber following an intrinsic atrial event, in response to the PV interval expiring without an intrinsic ventricular event being detected during the PV interval, during a period that the PMT has not been detected; and wherein the intrinsic atrial event can be the intrinsic atrial event that the aLP informs the vLP about via the i2i communication.

6. The method of claim 1, further comprising the vLP detecting an intrinsic ventricular event during the PMT PV interval, and in response thereto the vLP:

terminating the PMT PV interval; and informing the aLP, via an i2i communication, of the detected intrinsic ventricular event.

7. The method of claim 1, wherein:

the step of one of the aLP or the vLP detecting the PMT comprises the aLP detecting the PMT;

the step of the one of the aLP or the vLP that detected the PMT informing the other one of the aLP or the vLP comprises the aLP informing the vLP, via an i2i communication, that the PMT was detected;

the step of the aLP initiating a PMT PA interval comprises the aLP, in response to the aLP detecting the PMT, initiating the PMT PA interval that is shorter than the PA interval that the aLP would otherwise use for atrial pacing if the PMT was not detected; and the step of the vLP initiating a PMT PV interval comprises the vLP, in response being informed by the aLP that the PMT was detected, initiating the PMT PV interval that is longer than the PMT PA interval.

8. The method of claim 1, wherein:

the step of one of the aLP or the vLP detecting the PMT comprises the vLP detecting the PMT;

the step of the one of the aLP or the vLP that detected the PMT informing the other one of the aLP or the vLP comprises the vLP informing the aLP, via an i2i communication, that the PMT was detected;

the step of the aLP initiating a PMT PA interval comprises the aLP, in response to being informed by the vLP that the PMT was detected, initiating the PMT PA interval that is shorter than the PA interval that the aLP would otherwise use for atrial pacing if the PMT was not detected; and the step of the vLP initiating a PMT PV interval comprises the vLP, in response the vLP detecting the PMT, initiating the PMT PV interval that is longer than the PMT PA interval.

9. The method of claim 1, wherein the PMT PV interval equals the PMT PA interval plus a delay, and wherein the delay comprises either a fixed value or a rate dependent value.

10. The method of claim 1, wherein the PMT PA interval comprises a fixed value or a rate dependent value.

11. An implantable system configured to terminate a pacemaker mediated tachycardia (PMT), the implantable system comprising:

an atrial leadless pacemaker (aLP) configured to be implanted in or on an atrial cardiac chamber, the aLP including at least one processor and including at least two electrodes that can be used for sensing an intrinsic atrial event and pacing the atrial cardiac chamber;

a ventricular leadless pacemaker (vLP) configured to be implanted in or on a ventricular cardiac chamber, the vLP including at least one processor and including at least two electrodes that can be used for sensing an intrinsic ventricular event, pacing the ventricular cardiac chamber, and performing i2i communication;

wherein during a period that the PMT is not detected the aLP is configured to deliver an atrial pacing pulse to the atrial cardiac chamber in response to a PA interval expiring without an intrinsic atrial event being detected during the PA interval;

at least one of the aLP or the vLP configured to detect a PMT, and in response thereto, inform the other one of the aLP or the vLP, via an i2i communication, that the PMT was detected;

the aLP configured to initiate a PMT PA interval, in response to the PMT being detected, wherein the PMT PA interval is shorter than a PA interval that the aLP would otherwise use for atrial pacing if the PMT was not detected; and the vLP configured to initiate a PMT PV interval, in response to the PMT being detected, wherein the PMT PV interval is longer than the PMT PA interval;

wherein the PA interval specifies when an atrial pacing pulse should be delivered by the aLP to the atrial cardiac chamber following an intrinsic atrial sensed event, in response to the PA interval expiring without another intrinsic atrial event being detected during the PA interval, during a period that the PMT has not been detected;

wherein the PMT PA interval specifies when an atrial pacing pulse should be delivered by the aLP to the atrial cardiac chamber following an intrinsic atrial sensed event, in response to the PMT PA interval expiring without another intrinsic atrial event being detected during the PMT PA interval, during a period that the PMT has been detected; and wherein the PMT PV interval specifies when a ventricular pacing pulse should be delivered by the vLP to the ventricular cardiac chamber following an intrinsic atrial sensed event, in response to the PMT PV interval expiring without an intrinsic ventricular event being detected during the PMT PV interval, during a period that the PMT has been detected.

12. The implantable system of claim 11, wherein the aLP is configured to perform the following, in response to the PMT PA interval expiring without an intrinsic atrial event being detected during the PMT PA interval:

pace the atrial cardiac chamber; and inform the vLP, via an i2i communication, of the pacing the atrial cardiac chamber.

13. The implantable system of claim 12, wherein the vLP is configured to perform the following, in response to receiving the i2i communication from the aLP that informs the vLP of the pacing the atrial cardiac chamber:

terminate the PMT PV interval; and initiate an atrioventricular (AV) interval;

wherein the AV interval specifies when a ventricular pacing pulse should be delivered by the vLP to the ventricular cardiac chamber following a paced atrial event, in response to the AV interval expiring without an intrinsic ventricular event being detected during the AV interval, during a period that the PMT has not been detected; and wherein the paced atrial event can be the pacing of the atrial cardiac chamber that the aLP informs the vLP about via the i2i communication.

14. The implantable system of claim 11, wherein the aLP is configured to perform the following, in response to an intrinsic atrial event being detected during the PMT PA interval:

terminate the PMT PA interval; and inform the vLP, via an i2i communication, of the detected intrinsic atrial event.

15. The implantable system of claim 14, wherein the vLP is configured to perform the following, in response to receiving the i2i communication from the aLP that informs the vLP of the intrinsic atrial event being detected:

terminate the PMT PV interval; and initiate a PV interval;

wherein the PV interval specifies when a ventricular pacing pulse should be delivered by the vLP to the ventricular cardiac chamber following an intrinsic atrial event, in response to the PV interval expiring without an intrinsic ventricular event being detected during the PV interval, during a period that the PMT has not been detected; and wherein the intrinsic atrial event can be the intrinsic atrial event that the aLP informs the vLP about via the i2i communication.

16. The implantable system of claim 11, wherein the vLP is configured to perform the following, in response to an intrinsic ventricular event being detected during the PMT PV interval:

terminate the PMT PV interval; and inform the aLP, via an i2i communication, of the detected intrinsic ventricular event.

17. The implantable system of claim 11, wherein the aLP is configured to detect a PMT and configured to inform the vLP, via an i2i communication, that the PMT was detected.

18. The implantable system of claim 11, wherein the vLP is configured to detect a PMT and configured to inform the aLP, via an i2i communication, that the PMT was detected.

19. The implantable system of claim 11, wherein the PMT PV interval equals the PMT PA interval plus a delay, and wherein the delay comprises either a fixed value or a rate dependent value.

20. The implantable system of claim 11, wherein the PMT PA interval comprises a fixed value or a rate dependent value.

\* \* \* \* \*